US006391011B1

(12) United States Patent
Davis et al.

(10) Patent No.: US 6,391,011 B1
(45) Date of Patent: May 21, 2002

(54) SANITARY NAPKIN HAVING IMPROVED FLAP DISPOSITION AND MEANS FOR MAINTAINING THE FLAPS THEREIN

(75) Inventors: Elizabeth Jean Davis; Thomas Ward Osborn, III, both of Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 08/437,251

(22) Filed: May 8, 1995

Related U.S. Application Data (60) Continuation of application No. 08/082,894, filed on Jun. 25, 1993, now abandoned, which is a continuation of application No. 07/960,574, filed on Oct. 13, 1992, now abandoned, which is a continuation of application No. 07/732,442, filed on Jul. 18, 1991, now abandoned, which is a division of application No. 07/517,104, filed on May 1, 1990, now abandoned.

(51) Int. Cl.[7] .............................. A61F 13/15; A61F 13/20
(52) U.S. Cl. .............................. 604/385.05; 604/385.04; 604/385.201; 604/387
(58) Field of Search ...................... 604/385.1, 385.2, 604/386–387, 389–390, 385.01–385.05, 385.13, 385.201; 438/438–440

(56) References Cited

U.S. PATENT DOCUMENTS

| | | | | |
|---|---|---|---|---|
| 3,642,001 A | * | 2/1972 | Saber | 604/390 |
| 3,688,771 A | * | 9/1972 | Werner | 604/390 |
| 4,285,343 A | * | 8/1981 | McNair | 604/387 |
| 4,312,085 A | | 1/1982 | Potter | |
| 4,380,450 A | | 4/1983 | Reich | 604/386 |
| 4,402,689 A | | 9/1983 | Baum | 604/387 |
| 4,518,451 A | | 5/1985 | Luceri et al. | |
| 4,551,145 A | * | 11/1985 | Ryan | 604/389 |
| 4,608,047 A | | 8/1986 | Mattingly | 604/387 |
| 4,701,178 A | | 10/1987 | Glaug et al. | 604/387 |
| 4,735,316 A | * | 4/1988 | Froidh et al. | 206/438 |
| 4,759,754 A | | 7/1988 | Korpman | 604/387 |
| 4,765,477 A | * | 8/1988 | Froidh et al. | 206/438 |
| 4,846,828 A | * | 7/1989 | Mendelsohn | 604/387 |
| 5,037,417 A | * | 8/1991 | Ternstrom et al. | 604/389 |

FOREIGN PATENT DOCUMENTS

| | | | | |
|---|---|---|---|---|
| DE | 3326026 | * | 2/1985 | 604/389 |
| EP | 0299532 | * | 1/1989 | 604/385.1 |
| EP | 0313426 | * | 4/1989 | 604/387 |
| EP | 89/02729 | | 4/1989 | |
| EP | WO 89/027289 | | 4/1989 | |
| EP | 0345703 | * | 12/1989 | 604/387 |
| EP | 0 350 924 | | 1/1990 | |

* cited by examiner

*Primary Examiner*—John G. Weiss
*Assistant Examiner*—K. M. Reichle
(74) *Attorney, Agent, or Firm*—Edward J. Milbrada; Jeffrey V. Bamber; Steven W. Miller (57) ABSTRACT

Disclosed is a sanitary napkin having flaps folded over the topsheet. This arrangement helps to maintain the topsheet in a sanitary condition and is more convenient for the wearer than a configuration having the flaps folded over the backsheet. The flaps may be maintained in this folded arrangement by a unitary release strip which bridges the flaps and covers any adhesive used to attach the flaps to the undergarment. If desired, the release paper may further wrap the longitudinal side margins of the sanitary napkin to additionally cover adhesive disposed on the central portion of the backsheet. If desired, the flaps may be folded over the topsheet, overlap each other and be adhesively joined to the other flap.

6 Claims, 3 Drawing Sheets

SANITARY NAPKIN HAVING IMPROVED FLAP DISPOSITION AND MEANS FOR MAINTAINING THE FLAPS THEREIN

This is a continuation of application Ser. No. 08/082,894, filed Jun. 25, 1993, abandoned, which is a continuation of application Ser. No. 07/960,574, filed Oct. 13, 1992, abandoned, which is a continuation of application Ser. No. 07/732,442, filed Jul. 18, 1991, abandoned, which is a division of application Ser. No. 07/517,104, filed May 1, 1990, abandoned.

FIELD OF THE INVENTION

This invention is directed to sanitary napkins, and particularly to sanitary napkins having flaps. More particularly, this invention is directed to the packaging of such sanitary napkins prior to first use by the wearer.

BACKGROUND OF THE INVENTION

Sanitary napkins having flaps extending outwardly from the longitudinal side margins are well known in the art. For example, U.S. Pat. No. 4,589,876 issued May 20, 1986, to Van Tilburg and U.S. Pat. No. 4,687,478 issued Aug. 18, 1987, to Van Tilburg disclose preferred sanitary napkins with flaps and are incorporated herein by reference to illustrate particularly preferred flapped sanitary napkin constructions.

To conserve space during packaging, i.e., the period between manufacture of the sanitary napkin and its intended first use by the wearer, the flaps of such sanitary napkins are typically folded to overlay the backsheet. At the time of the first use by the wearer, the flaps are usually unfolded to facilitate installation of the sanitary napkin into the wearer's undergarment. Typically adhesive, interposed between the backsheet and the flap adhesive release paper, is used for maintaining the flaps in the folded disposition prior to the wearer's first use of the sanitary napkin.

Several attempts have been made to provide alternative means for maintaining the flaps in the desired disposition prior to first use of the sanitary napkin by the wearer. For example, U.S. Pat. No. 4,759,754 issued Jul. 26, 1988, to Korpman discloses an adhesive tab which can be used for maintaining the flaps in the desired disposition overlaying the backsheet during packaging. U.S. Pat. No. 4,701,178 issued Oct. 20, 1987, to Glaug et al. discloses a sanitary napkin having a single release strip which covers the centrally located adhesive of the backsheet and over which release strip the flaps are folded.

However, none of these attempts to improve packaging prior to the first use by the wearer have proven entirely satisfactory. For example, the wearer is typically concerned with maintaining the cleanliness, sanitary condition and appearance of the sanitary napkin's body contacting topsheet, rather than that of the sanitary napkin's garment contacting backsheet.

Further, when the wearer installs the sanitary napkin into her underwear, the sanitary napkin is typically in the wearing position, with the topsheet facing the wearer, while she manipulates the flaps and release strip. There can be an inconvenience associated with manipulating flaps and any associated release strip which are folded over the backsheet. Flaps folded over the backsheet are behind and obscured by the sanitary napkin, so that the flaps cannot be seen while the wearer is attempting to install the sanitary napkin to her undergarment. Also, flaps folded over the backsheet have a tendency to become adhered to the adhesive of the backsheet, unless held apart.

Accordingly, it is an object of this invention to overcome certain problems of the prior art. Particularly, it is an object of this invention to provide a flap disposition which promotes the cleanliness of the topsheet of the sanitary napkin during packaging and handling by the wearer prior to the first use of the sanitary napkin. Additionally, it is an object of this invention to provide a convenient means for manipulating the flaps from the packaged arrangement to the disposition which the flaps will be used during wear. Finally, it is an object of this invention to provide a effical process for making a sanitary napkin according to this invention.

BRIEF SUMMARY OF THE INVENTION

This invention comprises a sanitary napkin having and generally bounded by two longitudinal and two lateral side margins. The sanitary napkin has a liquid pervious topsheet, a liquid impervious backsheet that is at least partially peripherally joined to the topsheet, and an absorbent core between the topsheet and the backsheet. A flap extends laterally outwardly from each longitudinal side margin of the sanitary napkin and is folded over to the topsheet prior to the first use of the sanitary napkin by the wearer.

Several means are available for maintaining the flaps in this disposition. For example, flaps are typically provided with adhesive on the face of the flaps which is generally coextensive of the backsheet, and which adhesive is used to releasably affix the flaps to the undergarment of the wearer. A very suitable means for maintaining the flaps in the folded disposition having a topsheet facing relationship is a unitary release strip bridging such adhesive of the flaps.

BRIEF DESCRIPTION OF THE DRAWINGS

While the Specification concludes with claims particularly pointing out and distinctly claiming the present invention, it is believed the invention will be better understood from the following description taken in conjunction with the accompanying drawings wherein like parts are given the same reference numeral, analogous parts are designated with a prime symbol, related parts are designated by alphabetic characters, adhesive is shown in phantom and:

DETAILED DESCRIPTION OF THE INVENTION

Figure 1:
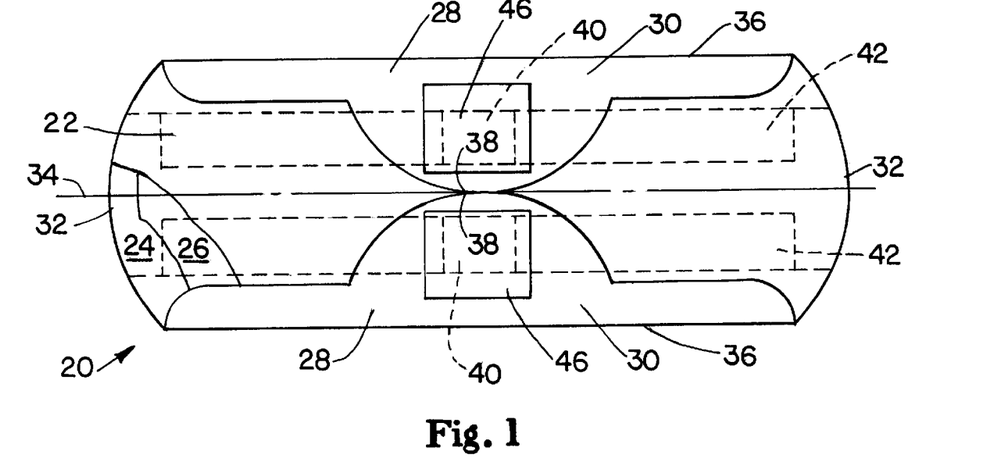
FIG. 1 is a top plan view, shown partially in cutaway, of a sanitary napkin according to the present invention.

As shown in FIG. 1, the invention comprises a disposable absorbent article, particularly a sanitary napkin 20. The sanitary napkin 20 is used to collect vaginal discharges, such as menses, and prevent soiling of the wearer's clothing by such discharges. The sanitary napkin 20 features a liquid pervious topsheet 22, a liquid impervious backsheet 24, an absorbent core 26 intermediate the topsheet 22 and the backsheet 24 and at least one flap 28 extending from a longitudinal side margin 30 of the sanitary napkin 20, and preferably two symmetrically opposite flaps 28, one extending from each longitudinal side margin 30 of the sanitary napkin 20. The perimeter of the sanitary napkin 20 is defined by two longitudinal side margins 30 and two lateral side margins 32.

Associated with the sanitary napkin 20 is a means, such as adhesive, for releasably affixing the sanitary napkin 20 to the undergarment of a wearer. More particularly, each flap 28 may have its own adhesive patch 40. Preferentially, such adhesive 40 is associated with the face of the flap 28 which contacts the undergarment of the wearer. Also the central portion of the sanitary napkin 20 intermediate the flaps 28 may have adhesive 42 associated with the area of the central portion of the sanitary napkin 20 which contacts the undergarment of the wearer. Preferentially such adhesive 42 is joined to the outwardly oriented face of the backsheet 24.

The sanitary napkin 20 has a longitudinal centerline 34 which conceptually divides the sanitary napkin 20 into two substantially symmetrically opposite halves. As used herein the term "longitudinal" refers to an imaginary line, axis or direction of the sanitary napkin 20, which line, axis or direction is typically centered between the longitudinal side margins 30 of the napkin and is generally aligned with the vertical plane which bisects a standing wearer into left and right body halves. The term "lateral" refers to an imaginary line, axis or direction generally orthogonal the longitudinal direction, within the plane of the sanitary napkin 20, and is generally sideways aligned relative to the wearer.

Examining the components in more detail with continuing reference to FIG. 1, the topsheet 22 is the component of the garment which is oriented towards and contacts the body of the wearer, and receives bodily discharges. The topsheet 22 is liquid pervious and should be flexible and nonirritating to the skin. As used herein the term "flexible" refers to materials which are compliant and readily conform to the shape of the body or respond by easily deforming in the presence of external forces. Preferably the topsheet 22 is not noisy, to provide discretion for the wearer. The topsheet 22 should be sanitary, clean in appearance and somewhat opaque to hide the bodily discharges collected in and absorbed by the core 26.

The topsheet 22 should further exhibit good strikethrough and rewet characteristics, permitting bodily discharges to rapidly penetrate the topsheet 22 to the core 26, but not flow back through the topsheet 22 to the skin of the wearer. Suitable topsheets 22 may be made from nonwoven materials or perforated polyolefinic films.

The topsheet 22 has a plurality of apertures to permit liquids deposited thereon to pass through to the core 26. Such apertures may, but need not, be present in the flaps 28. An apertured polyolefinic film topsheet 22 having about 5 to about 60 percent open area, typically about 25 percent open area, and a thickness of about 0.01 to about 0.05 millimeters prior to aperturing and about 0.46 to about 0.51 millimeters after aperturing is suitable.

If desired, the topsheet 22 may be sprayed with a surfactant to enhance fluid penetration to the core 26. The surfactant is typically nonionic and should be nonirritating to the skin. A surfactant density of about 0.01 milligrams per square centimeter of topsheet 22 area is suitable. A suitable surfactant is sold by the Glyco Chemical, Inc. of Greenwich, Conn. as Pegosperse 200 ML.

A particularly suitable topsheet 22 may be made in accordance with U.S. Pat. No. 4,342,314 issued Aug. 3, 1982 to Radel et al. and U.S. Pat. No. 4,463,045 issued Jul. 31, 1984 to Ahr et al., which patents are incorporated herein by reference for the purpose of disclosing particularly preferred executions of liquid pervious topsheets. A topsheet 22 made of model X-3265 or model P1552 apertured formed film sold by the Ethyl Corporation, Visqueen Division, of Terre Haute, Ind. has been found to work well.

The backsheet 24 may be any flexible, liquid resistant, preferably liquid impervious material, such as a polyolefinic film. The backsheet 24 prevents discharges collected by and contained in the sanitary napkin 20, and particularly discharges absorbed by the core 26, from escaping the sanitary napkin 20 and soiling the clothing and bedding of the wearer. Preferably the backsheet 24 is not noisy, to provide discretion for the wearer.

The backsheet 24 may also be impervious to malodorous gases generated by absorbed bodily discharges, so that the malodors do not escape and become noticed by the wearer. A low density polyethylene backsheet 24 about 0.01 to about 0.05 millimeters in thickness, preferably about 0.02 millimeters in thickness, has been found to work well. A polyethylene film, such as is sold by the Ethyl Corporation, Visqueen Division, under model XP-39385 has been found particularly well suited for the backsheet 24.

Further, the backsheet 24 may be made of a soft clothlike material which is hydrophobic relative to the topsheet 22, e.g., a polyester or polyolefinic fiber backsheet 24 works well. A particularly preferred soft, clothlike backsheet 24 material is a laminate of a polyester nonwoven material lamina and a film such as described in the aforementioned U.S. Pat. No. 4,476,180 issued to Wnuk.

In a particularly preferred embodiment, the backsheet 24 is slightly larger than the topsheet 22 and the intermediate absorbent core 26. In such an embodiment, the topsheet 22 and intermediate absorbent core 26 are peripherally circumscribed by the backsheet 24 which has a radial margin of about 0.5 centimeters to about 1.5 centimeters, preferably about 1.0 centimeter, from the side margins of the topsheet 22. This geometry provides a marginal area of protection should the core 26 become overloaded or the sanitary napkin 20 otherwise fail. In such an embodiment the backsheet 24 and flaps 28 are preferably unitary and coextensive.

The topsheet 22 and the backsheet 24 are preferentially peripherally joined using known techniques, either entirely so that the entire perimeter of the sanitary napkin 20 is circumscribed by such joinder or are partially peripherally joined at the perimeter. The term "joined" refers to the condition where a first member or component is affixed, or connected, to a second member or component either directly; or indirectly, where the first member or component is affixed, or connected, to an intermediate member or component which in turn is affixed, or connected, to the second member or component. The joined condition between the first member, or component, and the second member, or component, is intended to remain for the life of the sanitary napkin 20. Conversely, components are considered "removably affixed" if the components may be detached and separated from each other without destruction or unintended gross deformation of either.

Any joined arrangement that provides for capture of the core 26 intermediate the topsheet 22 and the backsheet 24 and a unitary assembly is suitable. Such an assembly has two mutually opposed major faces, one defined by the topsheet 22 and one defined by the backsheet 24.

The outwardly oriented face of the backsheet 24 may further comprise means 42 for attaching the sanitary napkin 20 to the undergarment of the wearer. Pressure sensitive adhesive 42 has been commonly found to work well for this purpose. Preferably a strip of longitudinally oriented adhesive 42 provides good protection against either the front or the back of the sanitary napkin 20 becoming detached from the wearer's undergarment. The adhesive strip 42 may be continuous or intermittent. A particularly preferred arrangement utilizes two longitudinally oriented strips 42, one on each side of the longitudinal centerline 34.

The absorbent core 26 is the means for collecting and containing bodily discharges, particularly menses, deposited thereon or which otherwise traverses through the liquid permeable topsheet 22. The core 26 is the component of the sanitary napkin 20 which receives and retains the bodily discharges. The core 26 is conformable and nonirritating to the skin. The core 26 may be rectangularly or hourglass shaped. The core 26 preferably has two opposed faces, one oriented towards the backsheet 24 and one oriented towards the topsheet 22.

Suitable materials for the core 26 include combinations of airfelt, such as cellulose wadding, and fibrated communition pulp; layers of tissue paper; and absorbent gelling materials. If a tissue paper core 26 is selected, tissue paper made in accordance with U.S. Pat. No. 4,191,609 issued Mar. 4, 1980 to Trokhan and incorporated herein by reference to show a particularly preferred tissue paper core construction for the sanitary napkin 20 described herein. If it is desired to incorporate absorbent gelling materials into the core 26 of the sanitary napkin 20, absorbent gelling materials made in accordance with U.S. Pat. No. Re. 32,649 issued Apr. 19, 1988 to Brandt et al., and incorporated herein by reference for showing particularly preferred absorbent gelling materials, are suitable. A suitable laminate of absorbent gelling materials and tissue may be purchased from the Grain Processing Corporation of Muscatine, Iowa under Model Number L535.

The core 26 need not have a total absorbent capacity much greater than the total amount of bodily discharges to be absorbed. The core 26 is preferably narrow and thin, to be comfortable to the wearer. For the embodiment described herein the capacity of the core 26 should be at least about 2 grams of 0.9 percent saline solution. Suitable saline solution is sold by Travenol Laboratories of Deerfield, Ill.

The core 26 should be sized to register with the topsheet 22 and backsheet 24. The core 26 is preferably interposed between the topsheet 22 and backsheet 24 to prevent the absorbent material of the core 26 from shredding or becoming detached while the sanitary napkin 20 is worn and to ensure proper containment of bodily discharges. This arrangement also helps to provide for a unitary assembly.

The sanitary napkin 20 preferably has a caliper of less than about 4 millimeters and more preferably less than about 2 millimeters, as measured with a comparator gage having an approximately 80.0 gram test weight, an approximately 10.0 gram comparator foot having a diameter of about 2.54 centimeters and a contact surface area of approximately 5.1 square centimeters. Also, the sanitary napkin 20 of the present invention should have a topsheet 22 surface area of at least about 100 square centimeters to prevent discharged fluids from missing the target area.

The core 26 is preferentially joined to the topsheet 22, and may be joined to the backsheet 24. Joining is preferentially accomplished by adhesive bonding the core 26 to the topsheet 22 or the backsheet 24. Such adhesive (not shown) may be applied in any suitable spray pattern, such as a spiral or longitudinally oriented beads. The adhesive should be surfactant resistant and of low pressure sensitivity, so as not to stick to the skin of the wearer.

The sanitary napkin 20 also comprises a flap 28 extending from a longitudinal side margin 30 of the sanitary napkin 20, and preferably one flap 28 extending from each longitudinal side margin 30 of the sanitary napkin 20. The flaps 28 have a proximal end 36 which is typically coincident with the juncture of attachment of the flap 28 to the longitudinal side margin 30 of the sanitary napkin 20 or, alternatively, the proximal end 36 of the flap 28 may be joined to the sanitary napkin 20 at any other location juxtaposed with the longitudinal side margin 30. The flaps 28 extend laterally outwardly from the sanitary napkin 20 and terminate at a distal end 38 which represents the point of the flap 28 furthest from the longitudinal axis 34 of the sanitary napkin 20. The flaps 28 may be of any shape desired, with one preferred shape being shown in FIG. 1.

The flaps 28 are laterally outboard of the longitudinal centerline 34 and central portion of the sanitary napkin 20. As used herein the phrase "central portion" refers to that part of the sanitary napkin 20 intermediate, particularly laterally intermediate, and defined by the proximal ends 36 of the flaps 28.

The flaps 28 may be comprised of an integral and contiguous extension of the topsheet 22, the backsheet 24, or a laminate of both. Alternatively, the flaps 28 may be made of a separate and independent piece of material joined to the longitudinal side margin 30 of the sanitary napkin 20.

Each flap 28 has one face generally coextensive of the topsheet 22 and a mutually opposed face generally coextensive of the backsheet 24. Faces are considered to be coextensive of the topsheet 22 or backsheet 24 if a line having a lateral component can be drawn from the central portion of the topsheet 22 or the backsheet 24 respectively, crosses a side margin 30 or 42 at the perimeter of the sanitary napkin 20, and intercepts such face.

The flaps 28 preferably have a means 40 for attaching one face of the flap 28 to the wearer's undergarment or to the other flap 28. The attachment means may be pressure sensitive adhesive 40. If pressure sensitive adhesive 40 is selected, it should be disposed on the face of the flap 28 generally coextensive of the backsheet 24 so that when the flaps 28 are wrapped around the crotch portion of the wearer's undergarment, the adhesive 40 will contact the outside of the wearer's undergarment. A generally rectangular patch of adhesive 40 on each flap 28, about 25 millimeters×20 millimeters in size works well. Suitable pressure sensitive adhesive 40 is sold by the Anchor Continental, Inc., 3 Sigma Division of Covington, Ohio as 0.02 millimeter pass with Century Adhesive A305-4.

For packaging, including shipment and sale, the flaps 28 are folded over the topsheet 22 so that the flaps 28 are in a disposition having the topsheet facing relationship of FIGS. 1–5. The flaps 28 are considered to be in a topsheet facing relationship if a line generally perpendicular to the plane of the sanitary napkin 20 is drawn outwardly from the topsheet 22 and intercepts either face of the flap 28. The flaps 28 are preferably, folded about the longitudinal lines generally coincident the proximal edges 36 of the flaps 28, so that the maximum area of the topsheet 22 may be covered by the flaps 28. This provides a larger area of the topsheet 22 which is protectively overlaid by the flaps 28, and particularly the area of the topsheet 22 which is generally registered with the wearer's vagina, so that a sanitary and clean appearance and condition of the topsheet 22 is maintained. It is not necessary that the flaps 28 be folded about the line generally coincident the proximal edge 36, that the, flaps 28 be in contacting relationship with the topsheet 22, or that no other folds between the distal and proximal ends 36 and 38 of the flaps 28 occur. It is only necessary that the flaps 28 face towards and cover the topsheet 22, help prevent outside contamination from readily soiling the portion of the topsheet 22 covered by the flaps 28 and the flaps 28 are manipulable to be readily unfolded by the wearer as the sanitary napkin 20 is installed in her undergarment.

Folding the flaps 28 in the configuration of FIG. 1 exposes the patch 40 of adhesive on the face of the flaps 28 generally coextensive of the backsheet 24. To prevent contamination and blocking of this patch 40, the adhesive patch 40 of each flap 28 may be covered with a separate and dedicated piece of release strip 46.

The various embodiments of release strips 46 described herein may be advantageously made of kraft paper, calendered paper, or any other materials well known in the art for such purpose. Machine glazed or machine finished paper having a basis weight of about $40.7 \times 10^{-3}$ kilograms per square meter (25 pounds/3,000 square feet) works well. However, the invention disclosed and claimed herein is by no means limited to any particular material selection.

Preferably the face of the release strip 46 which contacts the adhesive patches 40 has a release coating, such as silicone, to easily facilitate the removal of the release strip 46 from the flaps 28. Suitable release coatings are marketed by Akrosil of Menasha, Wis. as Silox 4R/0 and as Silox C1S.

If desired, the outwardly oriented face of the release strip 46 may further comprise indicia, such as advertising or wearer instructions, thereon. The use of indicia is even more advantageous with the unitary release strip 46' of FIG. 2, because of the increased visual impact presented by the larger surface area of such unitary release strip 46'.

Furthermore, the sanitary napkin 20 is preferably provided with a means for maintaining the flaps 28 in the topsheet facing relationship of FIG. 1 during packaging and prior to first use by the wearer. As used herein the "first use by the wearer" refers to the initial installation of the sanitary napkin 20 into the undergarment, so that the sanitary napkin 20 may begin to perform the intended function of collecting vaginal discharges.

One suitable means (not shown) for maintaining the topsheet facing relationship comprises a small patch of adhesive disposed on the face of each flap 28 generally coextensive of the topsheet 22. By contacting this, face of the flap 28 against the topsheet 22, the adhesive will adhere the flap 28 to the outwardly oriented face of the topsheet 22 until the flap 28 is detached by the wearer or premature, undesired separation occurs. Any adhesive FDA approved for contact with human skin is suitable. The adhesive may be either hot melt or preferably water based latex. Suitable adhesives are sold by the Findley Adhesives Company of Columbus, Ohio under the Model Nos. L8082-02 and H2128-01.

Figure 2:
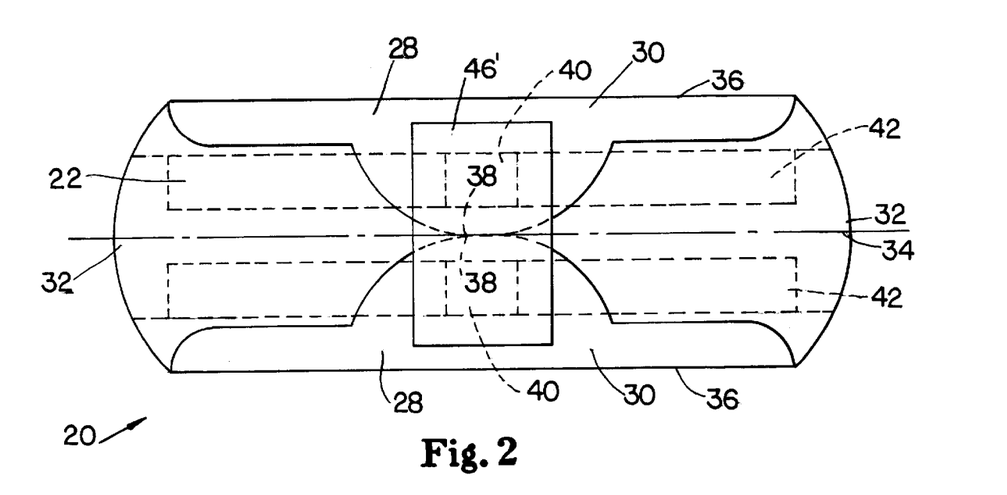
FIG. 2 is a top plan view of a sanitary napkin according to the present invention having a unitary release strip bridging the flaps.

Referring to FIG. 2, a more preferred means for maintaining the flaps 28 in the topsheet facing relationship is a unitary release strip 46' adhered to each patch 40 of adhesive on the flaps 28 and bridging both flaps 28. A component, such as a release strip 46', is considered "unitary" if it cannot be divided or disassembled without tearing or unintended gross separation. It is not necessary that a unitary component be made of a single material but, rather that such component cannot be disassembled from and subsequently reassembled into the original configuration. Components are considered to be "bridged" if they do not overlap and are connectively spanned by an independent component.

This unitary arrangement provides the advantage that the flaps 28 cannot be unfolded from the topsheet-facing relationship without detaching the unitary release strip 46' and, concomitantly advantageously, the adhesive patches 40 of the flaps 28 are covered.

Preferably, but not necessarily, the release strip 46', or at least the portion of the release strip 46' which bridges the flaps 28, is longitudinally bounded by the flaps 28. As used herein, a component or portion thereof is considered to be "longitudinally bounded" by the flaps 28 if such component or portion does not extend longitudinally outboard, i.e., away from the lateral centerline, of the flaps 28. By being longitudinally bounded by the flaps 28, the release strip 46' is prevented from having substantial contact with the topsheet 22 where adhesive attachment means are typically not disposed, and an economically advantageous conservation of material occurs.

It is important that the release strip 46' be conveniently and easily manipulated by the wearer. This is because the sanitary napkin 20 is frequently attached to the crotch of the wearer's undergarment when the release strip 46' is to be removed. With a sanitary napkin 20 having a unitary release strip 46' according to this invention, the wearer can see the flaps 28 in the advantageous topsheet facing relationship of FIGS. 1 and 2, can see the release strip 46' while it is being removed and can further see the flaps 28 and adhesive patches 40 thereon while they are being manipulated into the wearing arrangement to which the wearer is accustomed. The wearer attaches the central adhesive 42 to the crotch of her undergarment, peels off the release strip 46', typically starting at either lateral edge, folds the flaps 28 around the edges of the crotch of the undergarment, and attaches the flaps 28 to the outside of the undergarment using the flap adhesive 40.

In yet another embodiment (not shown) a tricomponent release strip 46' may be utilized. Such a release strip 46' has components made from a first material and which components are in contacting relationship with each adhesive patch 40. The first material components are then joined by a different second material which bridges the first material components and thus the flaps 28. This arrangement provides the advantage that less expensive materials may be utilized in the release strip 46'.

In a variant embodiment of FIG. 2 (not shown) the unitary release strip 46' may further comprise a means for initiating removal of the release strip 46' at or near its center, preferably at the longitudinal centerline 34, rather than initiate removal at either lateral edge of the release strip 46'. This may be accomplished, for example, by any appendage to the release strip 46' which enables it to be grasped near the longitudinal centerline 34 of the sanitary napkin 20. For example, the release strip 46' may be T-shaped in cross section having a tab which the user may grasp, or the release strip 46' may be looped upon itself to provide a double thickness of material which is not joined near the longitudinal centerline 34, and only joined near the lateral edges of the release strip 46'.

Figure 3:
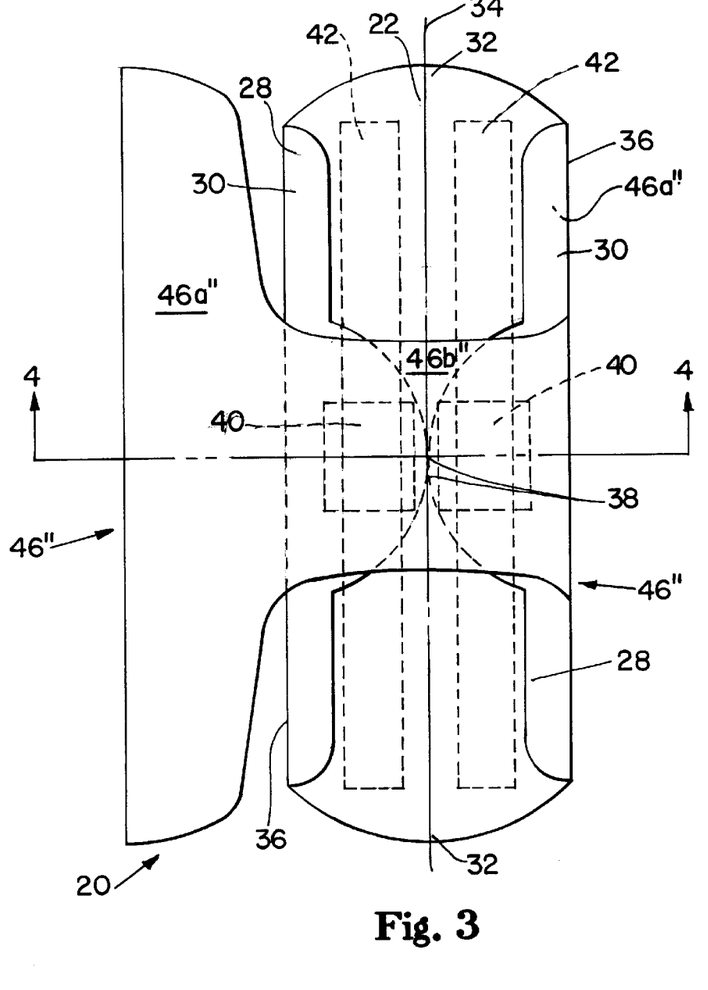
FIG. 3 is a top plan view of a sanitary napkin having an H-shaped release strip bridging the flaps and shown partially unwrapped for clarity.

Referring to FIG. 3, one nonlimiting variation of the aforementioned invention is a sanitary napkin 20 having a unitary H-shaped unitary release strip 46". This release strip 46" is preferably generally symmetric about the longitudinal centerline 34, and the lateral centerline of the sanitary napkin 20. The H-shaped release strip 46" has two substantially longitudinally oriented legs 46a" joined by a crossbar 46b". The crossbar 46b", as described relative to FIG. 2, bridges and is longitudinally bounded by the flaps 28 and covers the adhesive patches 40 joined to the outwardly oriented face of the flaps 28 generally coextensive of the backsheet 24. Either the crossbar 46b" or the legs 46a" may wrap the longitudinal side margins 30 of the sanitary napkin 20.

Figure 4:
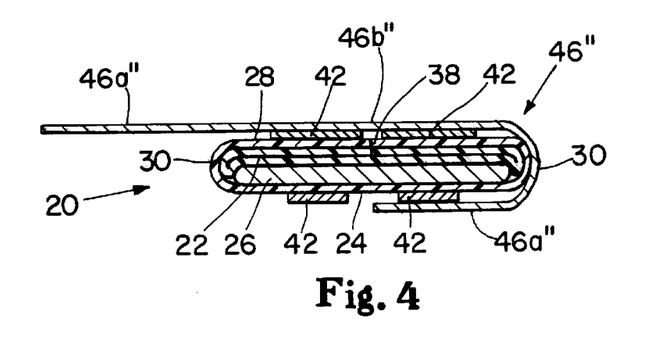
FIG. 4 is a vertical sectional view taken along line 4—4 of FIG. 3.

As illustrated by FIG. 4, this arrangement allows the legs 46a" of the release strip 46" to overlay the outwardly oriented face of the backsheet 24 and cover the adhesive strips 42 joined to the central portion of the backsheet 24. In this manner, a unitary release strip 46" performs the functions of maintaining the flaps 28 in the topsheet facing relation, covering the adhesive patches 40 of the flaps 28, and covering the adhesive patches 42 of the central portion of the backsheet 24.

To install the sanitary napkin 20, the wearer merely unwraps the legs 46a" of the release strip 46", exposing the backsheet 42 and the adhesive thereon. The wearer may then attach the central portion of the sanitary napkin 20 to the crotch of her undergarment, then detach the crossbar 46b" so that the flaps 28 are free to be unfolded. The sanitary napkin 20 may then be installed in the manner described above.

Figure 5:
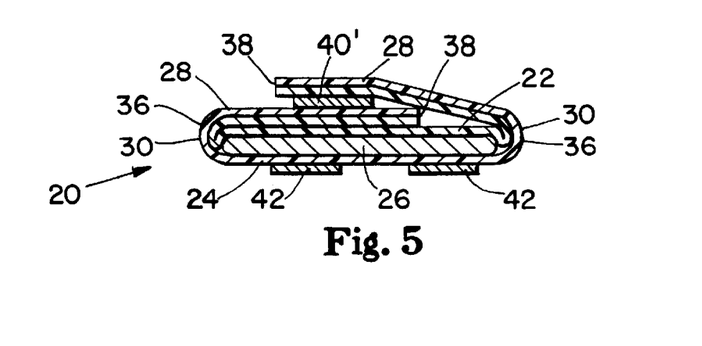
FIG. 5 is a vertical sectional view of a sanitary napkin according to the present invention having overlapping flaps.

Referring to FIG. 5, in yet another embodiment, the means for maintaining the flaps 28 in the topsheet facing relationship comprises mutually overlapping flaps 28 which are releasably affixed to each other. Disposed on the face of one flap 28, which face is generally coextensive of the backsheet 24, is a patch of adhesive 40'. The flap 28 having such adhesive 40' is the first flap 28, of the two flaps 28, to be folded over the topsheet 22 and is generally adjacent the topsheet 22 while folded. The second flap 28 is folded over the first flap 28.

In this configuration, the adhesive 40' of the first flap 28 may contact the face of the second flap 28 generally coextensive of the topsheet 22. It will be apparent that such adhesive 40' should be disposed on a portion of the first flap 28 which is overlapped by the second flap 28. In this manner, the opposed faces of each flap 28 are mutually releasably affixed by such adhesive 40' and the flaps 28 are maintained in the mutually overlapping, topsheet facing relationship. If desired, the adhesive 40' may be partially covered by a release strip (not shown).

Figure 6:
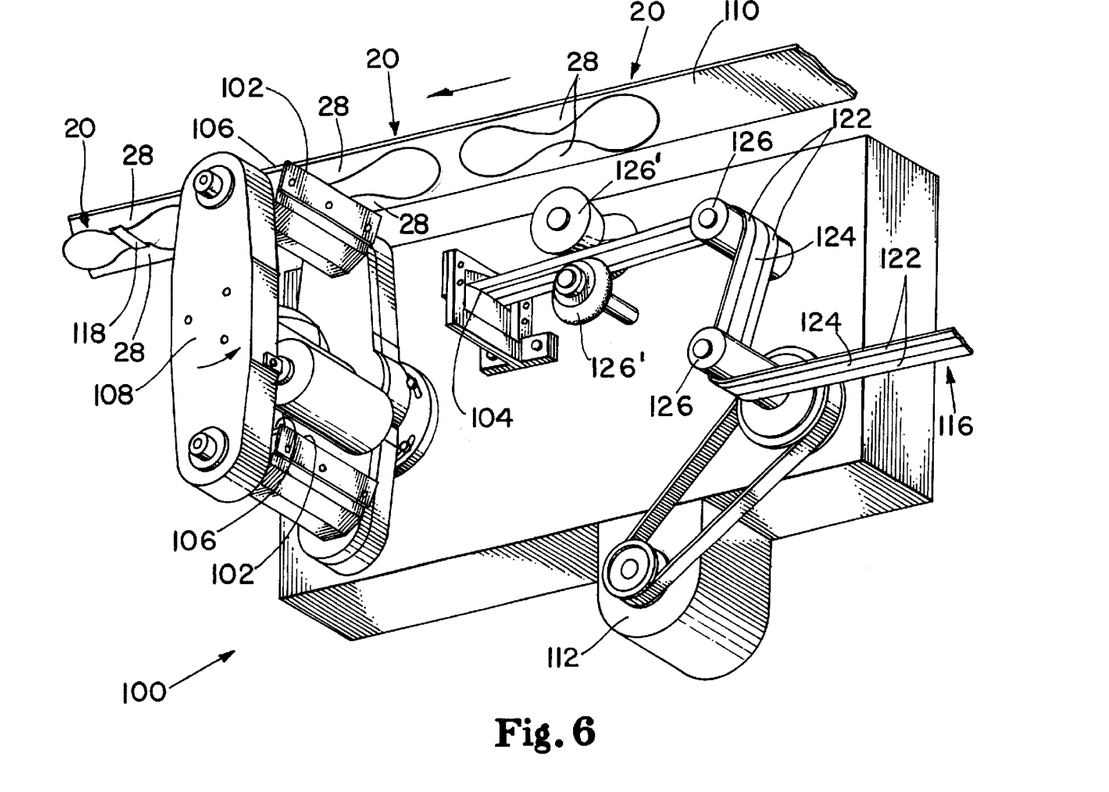
FIG. 6 is a schematic view of one apparatus which may be utilized to make a sanitary napkin according to the present invention.

Referring to FIG. 6, disclosed is an apparatus 100 and the associated process for carrying out the claimed invention. It is to be recognized that similar apparatus and processes are known and have been used in the art of applying adhesive 42 to the backsheet 24 of a sanitary napkin 20 having a conventional packaging disposition. More particularly, disclosed herein is a process for applying the adhesive 40 and release strip 46 to a sanitary napkin 20 provided in a generally flat, nonwrinkled disposition, with the flaps 28 prefolded into the aforementioned topsheet facing relationship, and the face of the flaps 28 generally coextensive of the backsheet 24 exposed to the apparatus 100.

The apparatus 100 comprises a conveyor 110, a means 112 for unwinding a roll of material 116; a means for cutting such material 116, such as a rotary knife 102 and a stationary anvil 104; and a means for transferring segments 118 of material 116 cut from the roll, such as a rotary vacuum head 106. The rotary knife 102 and rotary vacuum head 106 may be associated by and mounted on a rotating assembly 108. All of such components are synchronized to and used in conjunction with a production assembly line having a conveyor 110 that transports the sanitary napkins 20.

The apparatus is provided with a longitudinally trisectioned roll (not shown). As used herein a roll which is "longitudinally trisectioned" has three distinct zones, each laterally offset from the other. It will be apparent that the longitudinal direction of the roll of material 116 need not be coincident with the longitudinal direction of the sanitary napkin 20 to which a discrete segment 118 of the material from the roll is later applied.

The material 116 of the roll comprises any suitable release strip material 40 and adhesive 46, such as those described above. Preferably the parent material component of the roll comprises a release strip material 46 having mutually opposed first and second faces. The first face has two outboard trisections 122, each with a release coating, such as the aforementioned silicone, thereon. The two outboard trisections 122 are separated by a central trisection 124 intermediate the outboard trisections 122. The central section 124 may or may not have a release coating, as desired.

Each outboard trisection 102 is further provided with longitudinally oriented adhesive 40. The adhesive 40 may be continuous throughout the outboard trisections 122 or may be intermittent, as desired. The adhesive 40 may be applied by hot melting onto the roll 116 as it is unwound or, alternatively, the roll 116 may be precoated with the adhesive 40 prior to being wound into the rolled configuration. If the latter arrangement is selected, the release strip material 46 of roll 116 should be further release coated on the second face, so that the roll 116 does not stick to itself when the roll 116 is attempted to be unwound. Under either configuration, the release strip-adhesive combination 46 and 40 is unitary as provided by the roll 116.

Preferably, the discrete segments 118 have a pitch corresponding to the longitudinal dimension of the sanitary napkin 20. As herein "pitch" refers to the longitudinal distance between corresponding points of adjacent sanitary napkins 20 as they are transported on the conveyor 110. The conveyor 110 may be provided with a vacuum means (not shown) for temporarily holding the sanitary napkins 20 to the underside of conveyor 110. In this configuration, the flaps 28 of the sanitary napkins 20 may be downwardly folded over the topsheets 22 so that the faces of the flaps 28 generally coextensive of the backsheet 24 are exposed.

It is to be recognized a sanitary napkin 20 may be joined to or separated from the adjacent sanitary napkins 20 while on the conveyor 110. Thus, depending upon the final trimming of the sanitary napkin, the segments 108 cut from roll 116 may have a pitch less than or equal to that of the pitch of the sanitary napkins 20.

The process of supplying and segmenting material 116 from the roll may be accomplished by using the disclosed apparatus 100 as follows. The material 116 is fed from the roll (not shown) through the tracking and V-rolls 126 to the stationary anvil 104. The rotating assembly 108 comprises two oppositely disposed rotary knives 102 and two oppositely disposed rotary vacuum heads 106, so that for each one-half rotation of the rotary assembly 108, a sanitary napkin 20 may be manufactured according to the present invention.

Each rotary knife 102 and rotary vacuum head 106 is geared to the rotary assembly 108 in a known fashion, so that the rotary knife 102 and rotary vacuum head 106 face towards the conveyor 110 throughout the entire cycle. As the material 116 is fed to the stationary anvil 104, one rotary knife 102 cuts a segment 118 from the material 100. The segments 118 are cut to a predetermined length by the rotary knife 102 dependent upon the rotation frequency of the rotary knife 102 and speed at which the material 116 is fed from the roll through the stationary anvil 104. The length of a segment 118 cut from the trisectioned roll 116 preferably corresponds to the length of the segment 118 desired to be applied to the finished product, as illustrated in FIG. 2.

The cut segment 118 is held in the proper longitudinal orientation relative to the sanitary napkin 20 and transported from the stationary anvil 104 to the conveyor 110 by the rotary vacuum head 106. The segment 118 of adhesive 40 and release strip 46 is then generally contemporaneously applied to the exposed faces of the flaps 28 generally coextensive of the backsheet 24, so that the adhesive 40 of the cut segment 118 is in contacting relationship with such faces.

It will be apparent to one skilled in the art that several variations may be made without departure from the spirit and scope of the claimed invention. For example, asymmetric structures are possible, single flap sanitary napkins 20 are known in the art, and combinations of the aforementioned embodiments are feasible.

What is claimed is:

1. A sanitary napkin having flaps placed in a folded disposition prior to use, said sanitary napkin having longitudinal sides formed where said flaps are folded, said sanitary napkin comprising:

a central portion having a lateral centerline, two longitudinal side margins and two lateral side margins, a first end region extending from one of said lateral side margins a portion of the way toward said lateral centerline, a second end region extending from the other lateral side margin a portion of the way toward said lateral centerline, and a central region between said first and second end regions, said central portion comprising a liquid pervious topsheet, a liquid impervious backsheet joined to said topsheet, and an absorbent core positioned between said topsheet and said backsheet;

two flaps, one extending outwardly from each longitudinal side margin of said central portion and extending only from the central region of said central portion so that at least part of said central portion is laterally intermediate said flaps when said flaps are unfolded, said flaps each extending from a proximal edge adjacent the longitudinal side margins of said central portion, said flaps each having a region surrounding and including said proximal edges, and two opposed faces comprising a first face and a second face, said first face being inwardly-oriented toward said topsheet after said flaps are folded, and said second face being outwardly-oriented away from said topsheet after said flaps are folded, said flaps each being folded laterally inward along a single longitudinal axis in said region of the proximal edges of said flaps and being folded over said topsheet so that the inwardly-oriented face of at least one said flaps is directly in contact with said topsheet;

an adhesive patch on each outwardly-oriented second face of said flaps; and a unitary release strip bridging said adhesive patches on said second faces of said flaps for maintaining said flaps in said folded disposition, said release strip having two ends, wherein said ends of said release strip terminate short of the longitudinal sides of said folded sanitary napkin.

2. The sanitary napkin of claim 1 wherein the inwardly-oriented faces of both of said flaps are directly in contact with said topsheet.

3. The sanitary napkin of claims 1, or 2 wherein the central portion of said sanitary napkin is unfolded.

4. A sanitary napkin having flaps placed in a folded disposition prior to use, said sanitary napkin having a longitudinal centerline, a lateral centerline, and longitudinal sides formed where said flaps are folded, said sanitary napkin comprising:

a central portion having two longitudinal side margins, two lateral side margins, a first end region extending from one of said lateral side margins a portion of the way toward said lateral centerline, a second end region extending from the other lateral side margin a portion of the way toward said lateral centerline, and a central region between said first and second end regions, said central portion comprising a liquid pervious topsheet, a liquid impervious backsheet joined to said topsheet, and an absorbent core positioned between said topsheet and said backsheet;

two flaps, one extending outwardly from each longitudinal side margin of said central portion and extending only from the central region of said central portion so that at least part of said central portion is laterally intermediate said flaps when said flaps are unfolded, said flaps each extending from a proximal edge adjacent the longitudinal side margins of said central portion, said flaps each having two opposed faces comprising a first face and a second face, said first face being inwardly-oriented toward said topsheet after said flaps are folded, and said second face being outwardly-oriented away from said topsheet after said flaps are folded, said flaps each being folded over laterally inward along a single longitudinal axis generally coincident with the proximal edges of said flaps and being folded over said topsheet so that substantially the entire inwardly-oriented faces of both of said flaps are directly in contact with said topsheet;

an adhesive patch on each outwardly-oriented second face of said flaps; and a unitary release strip bridging said adhesive patches of said second faces of said flaps for maintaining said flaps in said folded disposition, said release strip having two ends, wherein said ends of said release strip terminate short of the longitudinal sides of said folded sanitary napkin.

5. A method of folding a sanitary napkin having flaps so that said flaps are maintained in a folded configuration prior to use, said method comprising the steps of:

(a) providing a sanitary napkin comprising a central portion and two flaps, said central portion having two longitudinal side margins and two lateral side margins, said central portion comprising a liquid previous topsheet, a liquid impervious backsheet joined to said topsheet, and an absorbent core positioned between said topsheet and said backsheet, one of said flaps extending outwardly from each longitudinal side margin of said central portion so that at least part of said central portion is laterally intermediate said flaps when said flaps are unfolded, said flaps each extending from a proximal edge adjacent the longitudinal side margins of said central portion, said flaps having a region surrounding and including said proximal edges, and said flaps each having two opposed faces comprising a first inwardly-oriented face and a second outwardly-oriented face wherein each second outwardly-oriented face has an adhesive patch thereon;

(b) folding said flaps laterally inward over said topsheet along a single longitudinal axis, said single longitudinal axis being located in the region of the proximal edges of said flaps so that the entire inwardly-oriented face of each of said flaps is oriented towards said topsheet and the inwardly-oriented face of at least one said flaps is directly in contact with said topsheet to provide a folded sanitary napkin having longitudinal sides formed where said flaps are folded wherein said longitudinal sides define the width of said folded sanitary napkin;

(c) exposing each said adhesive patch by said folding step;

(d) providing a unitary release strip for maintaining said flaps in said folded relationship, said unitary release strip having two ends and a length defined by the distance between said ends that is no greater than the width of said folded sanitary napkin; and (e) applying said unitary release strip to cover the exposed adhesive patches on said flaps when said flaps are in said folded relationship and maintain said flaps in said folded relationship, wherein said release strip is positioned so that the ends of said release strip terminate short of the longitudinal sides of said folded sanitary napkin.

6. A method of folding a sanitary napkin having flaps so that said flaps are maintained in a folded configuration prior to use, said method comprising the steps of:

(a) providing a sanitary napkin comprising a central portion and two flaps, said central portion having two longitudinal side margins and two lateral side margins, said central portion comprising a liquid pervious topsheet, a liquid impervious backsheet joined to said topsheet, and an absorbent core positioned between said topsheet and said backsheet, one of said flaps extending outwardly from each longitudinal side margin of said central portion so that at least part of said central portion is laterally intermediate said flaps when said flaps are unfolded, said flaps each extending from a proximal edge adjacent the longitudinal side margins of said central portion, said flaps having a region surrounding and including said proximal edges, and said flaps each having two opposed faces comprising a first inwardly-oriented face and a second outwardly-oriented face;

(b) folding said flaps laterally inward over said topsheet along a single longitudinal axis in the region of the proximal edges of said flaps so that said inwardly-oriented faces of said flaps are oriented towards said topsheet and the inwardly-oriented face of at least one said flaps is directly in contact with said topsheet to provide a folded sanitary napkin having longitudinal sides formed where said flaps are folded wherein said longitudinal sides define the width of said folded sanitary napkin;

(c) providing a unitary release strip for maintaining said flaps in said folded relationship, said unitary release strip having two ends, a length defined by the distance between said ends that is no greater than the width of said folded sanitary napkin, and an adhesive patch adjacent each of said ends; and (d) applying said unitary release strip with said adhesive patches thereon so that said adhesive patches will each adhere to one of said flaps and said release strip will cover the adhesive patches on said flaps when said flaps are in said folded relationship and maintain said flaps in said folded relationship, wherein said release strip is positioned so that the ends of said release strip terminate short of the longitudinal sides of said folded sanitary napkin.

* * * * *

UNITED STATES PATENT AND TRADEMARK OFFICE
CERTIFICATE OF CORRECTION

PATENT NO. : 6,391,011 B1
DATED : May 21, 2002
INVENTOR(S) : Davis et al.

It is certified that error appears in the above-identified patent and that said Letters Patent is hereby corrected as shown below:

Title page,
Item [63], Related U.S. Application Data, "division" and insert therefore
-- continuation --.
Item [57], ABSTRACT
Line 1, please delete "Disclosed is-a" and insert therefore -- A --.

Column 2,
Lines 22-29, please delete the entire second paragraph and insert therefore
-- The flaps are typically provided with adhesive on the face of the flaps which is generally coextensive of the backsheet, and which adhesive is used to releasably affix the flaps to the undergarment of the wearer. The flaps are maintained in the folded disposition by a unitary release strip bridging such adhesive of the flaps, the ends of the release strip terminating short of the longitudinal sides of the folded sanitary napkin. The invention further comprises methods of providing such sanitary napkins.--

Column 6,
Line 36, please delete "42", and insert therefor -- 32 --.
Line 59, after "preferably", please delete "," (the comma).

Column 7,
Line 1, after the second occurrence of "the", please delete "," (the comma).

Column 11,
Lines 41, 43 and 49, please delete "said flaps".
Lines 41, 43 and 49, after "each", please insert -- flap --.
Line 42, after "the", please insert -- associated --.
Line 42, please delete "margins" and insert therefor -- margin --.
Line 44, after "said", please insert -- respective --.
Line 44, please delete "edges" and insert therefore -- edge --.
Line 50, please delete "of".
Line 51, before "the", please insert -- surrounding and including --.
Line 51, before "being", please insert -- said flaps --.
Line 53, please delete "flaps" and insert therefore -- flap --.
Line 63, before "inwardly", please insert -- entire --.

UNITED STATES PATENT AND TRADEMARK OFFICE
CERTIFICATE OF CORRECTION

PATENT NO. : 6,391,011 B1
DATED : May 21, 2002
INVENTOR(S) : Davis et al.

It is certified that error appears in the above-identified patent and that said Letters Patent is hereby corrected as shown below:

Column 12,
Lines 23, 25, 30 and 57, please delete "said flaps".
Lines 23, 25, 30 and 57, after "each", please insert -- flap --.
Lines 24 and 58, after "the", please insert -- associated --.
Line 24, please delete "margins" and insert therefor -- margin --.
Lines 32, 60 and 67, please delete "edges", and insert therefor -- edge --.
Line 32, please delete "flaps", and insert therefor -- flap --.
Line 32, after "and", please insert -- said flaps --.
Line 50, please delete "previous" and insert therefor -- pervious --.
Line 59, please delete "said flaps", and insert therefor -- each flap --.
Line 60, after "said", please insert -- respective --.
Line 61, please delete "said flaps each having".
Lines 66-67, please delete "said single longitudinal' axis being located in the region of" and insert therefor -- in the region surrounding and including --.

Column 13,
Lines 1 and 3, please delete "flaps" and insert therefor -- flap --.

UNITED STATES PATENT AND TRADEMARK OFFICE
CERTIFICATE OF CORRECTION

PATENT NO. : 6,391,011 B1
DATED : May 21, 2002
INVENTOR(S) : Davis et al.

It is certified that error appears in the above-identified patent and that said Letters Patent is hereby corrected as shown below:

Column 14,
Line 2, please delete "said flaps".
Line 2, after "each", please insert -- flap --.
Line 3, after "the", please insert -- associated --.
Line 3, please delete "margins" and insert therefor -- margin --.
Lines 4, 11 and 14, please delete "said flaps" and insert therefor -- each flap --.
Line 5, after "said", please insert -- respective --.
Lines 5 and 11, please delete "edges" and insert therefor -- edge --.
Line 6, please delete "said flaps each having".
Line 9, after "folding", please insert -- each of --.
Line 9, after "topsheet", please inert --, each of said flaps being folded --.
Line 10, after "region", please insert -- surrounding and including --.
Line 10, please delete "of".

Signed and Sealed this

Twenty-fourth Day of August, 2004

JON W. DUDAS
*Director of the United States Patent and Trademark Office*